(12) United States Patent
Montagu

(10) Patent No.: US 7,199,360 B1
(45) Date of Patent: Apr. 3, 2007

(54) SYSTEM AND METHOD FOR CALIBRATING A FLUORESCENCE MICROSCOPE

(76) Inventor: Jean Montagu, 76 Walnut Pl., Brookline, MA (US) 02445

( * ) Notice: Subject to any disclaimer, the term of this patent is extended or adjusted under 35 U.S.C. 154(b) by 0 days.

(21) Appl. No.: 11/331,961

(22) Filed: Jan. 13, 2006

(51) Int. Cl.
*G01D 18/00* (2006.01)
(52) U.S. Cl. ............... 250/252.1; 250/458.1; 378/44
(58) Field of Classification Search ............. 250/252.1, 250/458.1
See application file for complete search history.

(56) References Cited

U.S. PATENT DOCUMENTS

| | | | | |
|---|---|---|---|---|
| 6,381,013 | B1* | 4/2002 | Richardson | 356/305 |
| 6,740,871 | B1* | 5/2004 | Staton et al. | 250/252.1 |
| 2003/0105195 | A1* | 6/2003 | Holcomb et al. | 524/102 |
| 2004/0125372 | A1* | 7/2004 | Walla et al. | 356/318 |
| 2004/0196455 | A1* | 10/2004 | Ermantraut et al. | 356/243.1 |
| 2004/0259260 | A1* | 12/2004 | Gunstream et al. | 249/126 |

OTHER PUBLICATIONS

"microscopy". Dorland's Illustrated Medical Dictionary (2003). Retrieved Nov. 20, 2006, from xreferplus. http://www.xreferplus.com/entry/4182525.*
"darkfield microscopy". Mosby's Medical, Nursing and Allied Health Dictionary (2002). Retrieved Nov. 20, 2006, from xreferplus. http://www.xreferplus.com/entry/3035128.*

* cited by examiner

*Primary Examiner*—Akm Ullah
*Assistant Examiner*—Jessica L Eley
(74) *Attorney, Agent, or Firm*—Cesari and McKenna LLP

(57) ABSTRACT

A system and method are provided to calibrate fluorescence detection of a fluorescence microscope by using a near-perfectly uniform reflector as a target in combination with temporary removal of the microscope's emission filter. Excitation light is reflected from the near-perfectly uniform reflector back into the microscope's objective optical system and transmitted to a dichroic. A small fraction of the excitation light passes though the dichroic and is measured by a CCD camera or other appropriate measurement device. By measuring the intensity of the residual excitation light at a plurality of points in the field of view, variations in illumination intensity may be determined. Using this, fluorescence detection at different points in the field of view may be readily calibrated.

15 Claims, 5 Drawing Sheets

SYSTEM AND METHOD FOR CALIBRATING A FLUORESCENCE MICROSCOPE

BACKGROUND OF THE INVENTION

1. Field of the Invention

The present invention relates generally to microscope calibration and more particularly to the calibration of fluorescence detection across a field of view of a fluorescence microscope.

2. Background Information

The fluorescence microscope has become a valuable tool in biology and biomedical science, as well as in material science and other fields, due to its unique detection abilities. Such detection abilities are a result of the microscope's method of operation. When an organic or inorganic specimen (a target) is exposed to intense light (termed excitation light) it will generally emit light (termed emission light), in the physical phenomenon of fluorescence. Emission light typically is very faint, having only an intensity between a hundred thousandth and a millionth the intensity of the excitation light. A fluorescence microscope operates by separating the faint emission light from any reflected excitation light, and thereafter measuring the emission light to identify structures in the target.

In modern microscopy, the excitation light is commonly generated by epi-florescence illumination, where light of a defined wavelength is applied to the target (an instrument operating in this manner is termed an epi-florescence microscope). By using a defined wavelength, excitation light may be more easily separated from the emission light. Further, in addition to measuring the natural fluorescence of the target (the auto-fluorescence), it is common to use fluorescent dies (fluorochromes) that attach to specific structures of the target and emit light of known wavelengths when excited. In such a manner, specific features of the target may be studied, for example the presence of particular molecules may be detected.

Fluorescence microscopy may be better understood through reference to FIG. 1, which is a schematic diagram of an exemplary fluorescence microscope 100. An illumination source 110 creates high intensity light that may be multispectral or limited to certain wavelengths. The illumination source is commonly an arc-discharge lamp, such as a mercury or xenon burner. Alternatively, the illumination source may be an integrated assembly of Light Emitting Diodes (LEDs) such as the Luxeon® Star LEDs available from Lumileds Lighting, LLC of San Jose, Calif. In other configurations, the illumination source may be a laser light source.

Light from the illumination source generally passes through one or more collimating lenses 120 that convert the illumination light into a collimated beam, whose rays are parallel to each other. An excitation filer 130, following the collimating lenses 120, selectively transmits a particular wavelength, or narrow band of wavelengths, and blocks light of other wavelengths. The transmitted wavelengths (now termed excitation light) enter an optical block 150 of the microscope 100. The excitation light generally enters the optical block 150 perpendicular to the optical axis of the microscope 100.

In the optical block 150, the excitation light is reflected by a dichromatic beam-splitting mirror 140 (called a dichroic). The dichroic 140 is tilted at a 45-degree angle with respect to the incoming excitation light and thus reflects the light downward into an objective optical system 160 toward a target 190. Typically, a shutter mechanism 195 is placed before the target, so that exposure time may be regulated. In a typical fluorescence microscope, the target is illuminated across a field of view of about ½ to 1 square centimeters. When the target is illuminated by the excitation light, it fluoresces (either through autofluorescence or due to the application of fluorochromes). Thereafter, florescence emission (emission light) from the illuminated target travels upwards and is collected by the objective optical system 160, now serving in its usual image-forming function. In addition to the emission light, large amounts of excitation light are reflected from the target and re-enter the objective optical system 160. The emission light and the excitation light reflected from the target are separated by the dichroic, which selectively reflects wavelengths associated with the excitation light back towards the illumination source, where they are dissipated. The emission light passes through the dichroic 140 to an emission filter 170 that suppresses residual excitation light. The emission light then enters an optical eyepiece assembly (not shown) for viewing by an operator, or enters an image sensing device 180, such as a Charge-Coupled Device (CCD) camera. The image sensing device 180 contains an array of sensors, each of which measures (samples) the light at a different point in the field of view to form a pixel (i.e. a small discrete component of a digital image). Digital images are typically composed of a large number of pixels, and image sensing devices often describe images using several million pixels (megapixels).

To fully exploit the capabilities of a florescence microscope, an adequate calibration technique is needed. Unfortunately, calibration of a florescence microscope is different from, and more demanding than, calibration of a conventional optical microscope, and is still an outstanding problem. Conventional optical microscopes are generally adequately calibrated by standardizing qualities such as resolution, contrast, depth of field, and distortion. To that end, calibration targets have been employed consisting of printed or vapor deposited patterns on substrates, such as glass or plastic slides.

Yet fluorescence microscopes also require calibration of fluorescence detection, permitting emission light intensity to be measured accurately across a field of view. That is, calibration is required so that the measured intensity differences across a field of view are due to differences in the target and not "irregularities" in the fluorescence microscope itself. Known calibration techniques have proven inadequate for this type of calibration.

Unwanted variation in emission light is primarily caused by variation in excitation light intensity, which can vary on the order of 3:1 between highs and lows across the field of view. Further unwanted variation is introduced by irregularities in the lenses of the optical path of the microscope. Such variation is generally not apparent when an image is observed by the human eye, as the human eye is a poor detector of intensity deviations. Yet, when an image is electronically captured and quantified, such variation is clearly apparent. Without an acceptable degree of calibration, "quantified fluorescent microscopy" (i.e. the assignment of numerical values to image characteristics) proves impracticable. Uncalibrated results may not readily be compared between instruments, or even between differing regions of a field of view of the same instrument.

One application adversely affected by a lack of calibration of fluorescence detection is the examination of biochips and microarrays, where target materials are affixed to a substrate in a 2-dimensional array of spots. Such microarrays are used in bioassay methodologies where a number of biologically identical spots are laid down upon the substrate, each being an independent assay. Statistical analysis across the array is typically used to increase accuracy. Yet, if there is considerable unwanted variation in emission light intensity, spots in differing location may not adequately be compared. Thus, without adequate calibration, the utility of this technique is reduced.

As stated above, existing techniques for calibrating fluorescence microscopes have not adequately addressed calibration of fluorescence detection across a field of view. With most prior techniques, fluorescence detection may not be calibrated to greater than a relative accuracy of 10%. As such, existing techniques are generally unsuitable for quantified fluorescent microscopy, where accuracies of 1% or greater are desired.

One existing calibration technique involves layering organic fluorescent material about 30 microns (micrometers) in thickness upon a non-fluorescent glass substrate, such as synthetic quartz. Since fluorescent material emits light throughout its thickness, for such a technique to be capable of intensity calibration to 1% accuracy, the thickness of the fluorescent material would need to be controlled to within 30 nanometers (nm). This is impractical given present manufacturing technology and economic constraints, and, accordingly, much lesser accuracy levels must be accepted.

Another existing technique for calibrating a fluorescence microscope involves a substrate of fluorescent glass on which a very thin patterned metal layer (such as a nickel layer) is deposited. While this general technique has been advantageously employed in the calibration of image resolution, it offers little precision in calibrating fluorescence detection. The glass substrate's emissions vary significantly throughout the field of view. Such variations are due to both thickness variations and non-uniformities in the glass's composition. Accuracy may be improved somewhat by depositing a thin layer of Kapton® film (available from DuPont High Performance Materials Inc.) on an opaque cover on the glass substrate. This improved technique is described in U.S. Pat. No. 6,472,671 to Montagu, issued on Oct. 29$^{th}$, 2002, which is incorporated herein by reference in its entirety. Use of a Kapton® film may allow thickness variations in the fluorescence source to be reduced to 0.1 micron. Yet this is still insufficient for high accuracy calibration.

A wide variety of other calibration techniques involving calibration targets, surfaces, and coatings are commercially available. Yet, absent the use of exotic and cost-prohibitive materials and manufacturing methods, these techniques are unable to achieve a relative accuracy in emission intensity measurement greater than about 10%. What is needed is a relatively simple and inexpensive system and method for calibrating a fluorescence microscope that allows one to calibrate fluorescence detection across the entire field of view of a microscope to an acceptable level of accuracy. Such a system and method would be highly advantageous to the field of quantified fluorescence microscopy.

SUMMARY OF THE INVENTION

Unlike prior calibration techniques that attempted to provide a near-perfectly uniform fluorescent emitter target (which has proven impractical), the present technique uses a near-perfectly uniform reflector target in combination with the temporary removal of the microscope's emission filter. Using the present invention, variations in excitation light may be measured to a high degree of accuracy (on the order of 1%), and then used to calibrate the detection of emission light to a similar degree of accuracy.

Specifically, when a near-perfectly uniform reflector target is used, excitation light is reflected back into the microscope's objective optical system, and transmitted to the dichroic. Generally, commercially available dichroics are imperfect in separating excitation light reflected from the target from emission light, allowing a small fraction of the excitation light to pass there-through (this light is termed herein "residual excitation light"). Accordingly, fluorescent microscopes typically employ an emission filter to block the residual excitation light. The present invention capitalizes on the imperfection of a dichroic. By temporarily removing the emission filter the residual excitation light is incident upon, and may be measured by, an image recording device, such as a CCD camera, attached to the microscope. The intensity of the residual excitation light is measured at a large number of points in the field of view, and stored as pixels of a digital image. This digital image may be considered a "map" of intensity levels of residual excitation light. Such a "map" captures errors introduced by the illumination source, collimating lenses, and the optical path of the microscope. Any errors that would be caused by the emission filter itself (which has been removed) are negligible and thus may be ignored. Alternatively, these errors may be determined independently using well-known techniques. Similarly, any errors introduced by the fact that the excitation and emission light are of differing wavelengths may also be ignored as negligible.

Using the "map" of intensity levels of residual excitation light, a map of "correction factors" is calculated, with an individual correction factor associated with each point (pixel of an image) of the field of view. Since fluorescence emission is related to the intensity of the excitation light, "correction factors" may be readily calculated by scaling the residual excitation light measurements. Thereafter the emission filter of the microscope may be replaced and a measurement of a desired target taken. The recorded image of the target is adjusted according to the "correction factors" to compensate for the irregularities in the microscope. In this way, fluorescence detection calibration may be achieved.

In an alternate embodiment, a neutral density filter is inserted in the optical path of the microscope in place of the temporarily removed emission filter. A neutral density filter is advantageously used when the normal exposure time cannot be controlled to an acceptable level of accuracy. The neutral density filter blocks a portion of the residual excitation light and thus allows a longer than normal (and thus a more accurately measurable) exposure time to be used in calibration. As with the excitation filter, the properties of the neutral density filter may be determined independently and incorporated into the calibration result.

In yet another embodiment, a control calibration chip is created in connection with the above technique. A control calibration chip is a target of robust mechanical and optical properties that is specifically associated with a particular fluorescence microscope. An image of the chip is generated when the microscope is in proper calibration and the chip and image are both retained with the microscope. To verify or adjust calibration at a later date, the chip is re-imaged and the new image compared to the retained earlier image.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
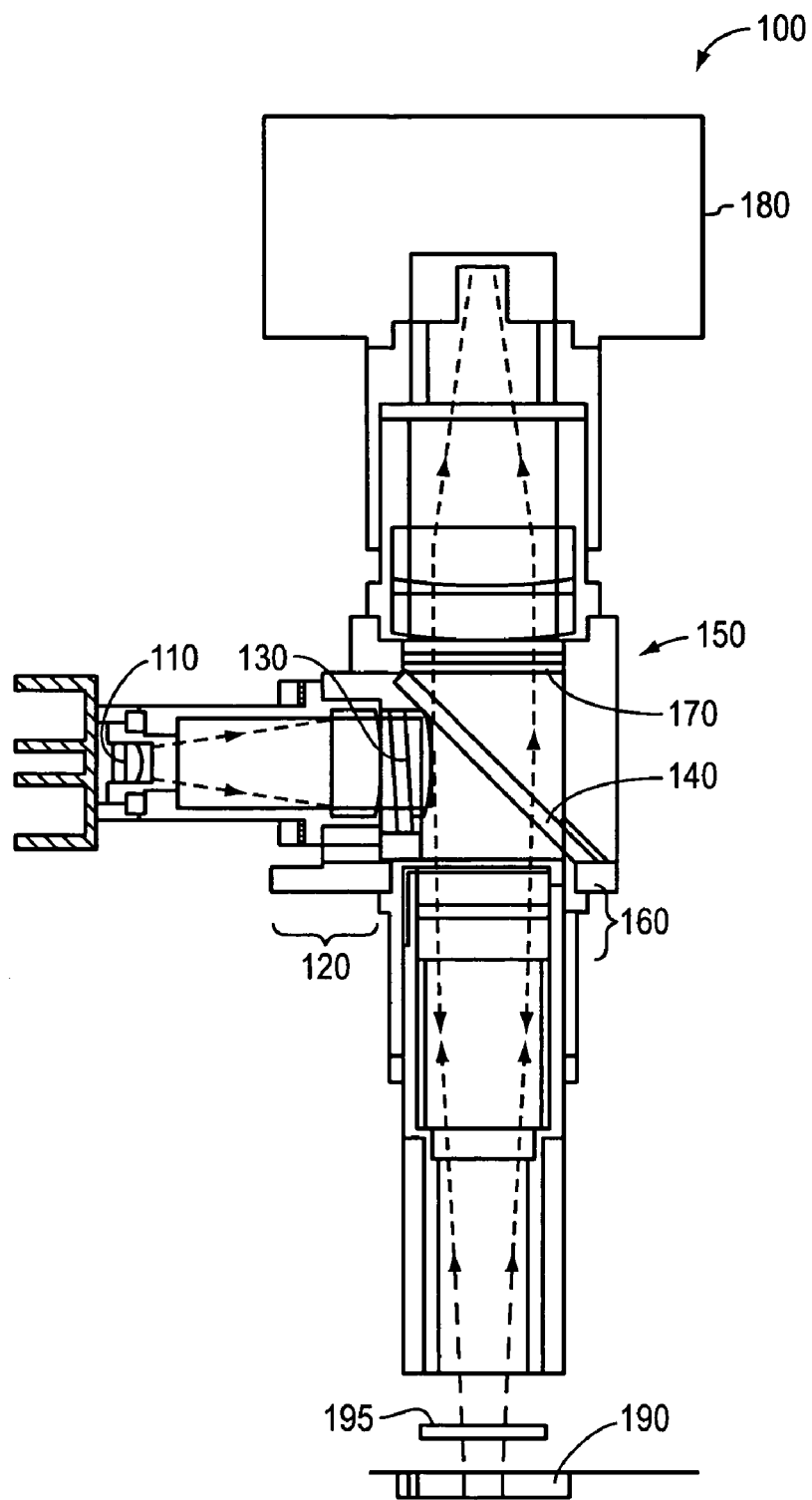
FIG. 1 is a schematic diagram of an exemplary fluorescence microscope.

Throughout the description below, reference will be periodically made to structures depicted in FIG. 1. The reader is encouraged to refer to FIG. 1 when structures shown in FIG. 1 are discussed.

Figure 2:
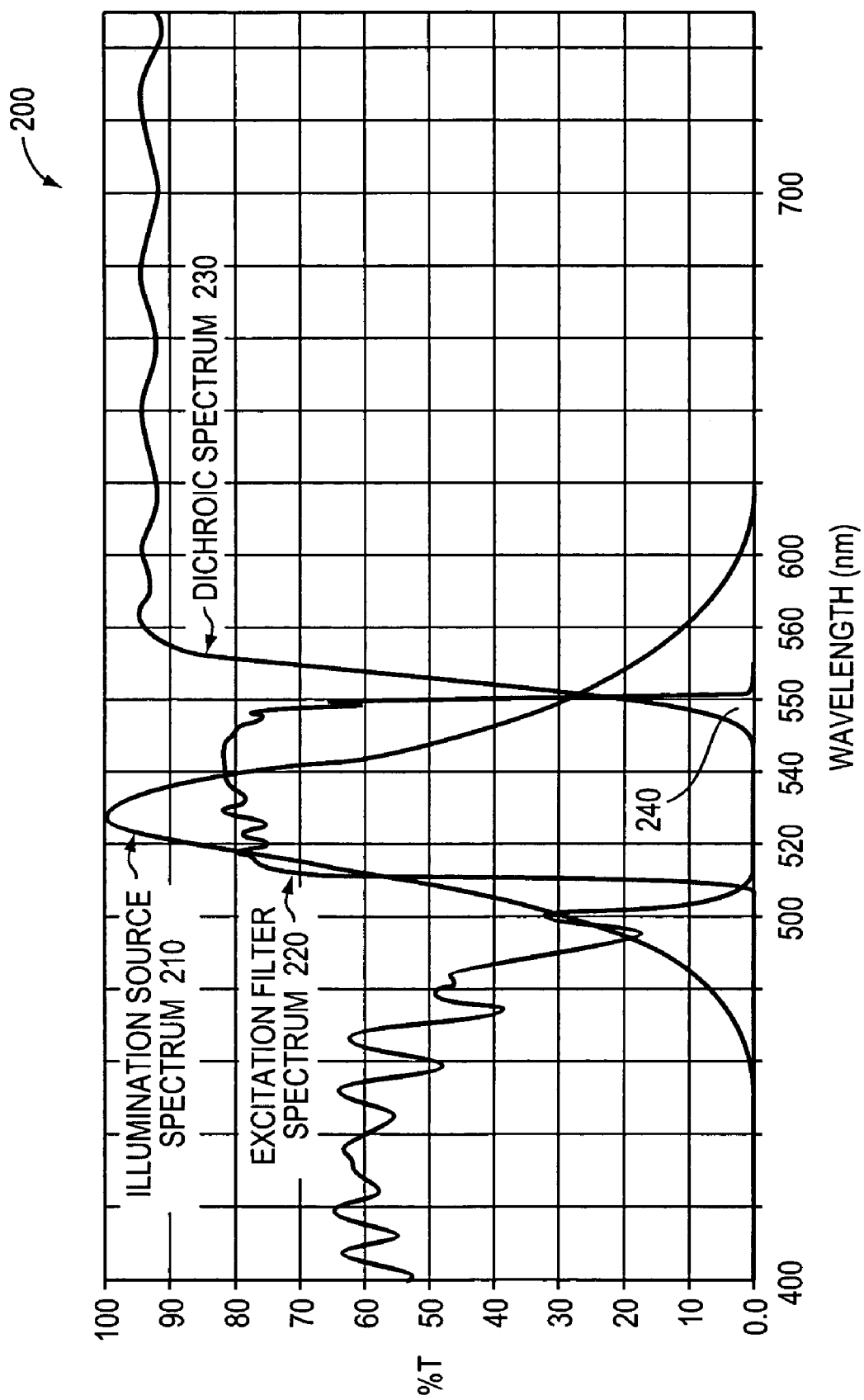
FIG. 2 is graph depicting an exemplary excitation spectrum, dichroic spectrum, and illumination source spectrum for an exemplary fluorescence microscope.

FIG. 2 is a graph depicting an exemplary illumination source spectrum 210, excitation filter spectrum 220 and dichroic spectrum 230 for an exemplary fluorescence microscope. Such spectrums are representative of one possible selection of components, for example, selection of a HQ535/50x Excitation filter and a Q565LP Dichroic, both available from Chroma Technology Corp. Typically, the illumination source 110 of a fluorescence microscope 100 produces multi-spectral light across a range of wavelengths. For example, FIG. 2 depicts an exemplary illumination source spectrum 210 spanning wavelengths from approximately 460 nanometer (nm) to 620 nm, with an intensity peak at approximately 530 nm. An excitation filter 130 is generally employed in the microscope to reduce the illumination light to a narrower band of wavelengths. In this example, the excitation filter 130 serves to restrict transmission of light mainly to wavelengths between 510 nm and 560 nm, as shown by the excitation filter spectrum 220. Excitation light that passes through the excitation filter is directed upon the target by a dichroic 140. Significant excitation light is reflected back by the target to the dichroic, where it is separated from the emission light. For typical target materials, the excitation light that is reflected back by the target has about 10% of the intensity as the original excitation light.

Most commercially available dichroics are imperfect in separating reflected excitation light, allowing a fraction of the light to pass there-through (this light is herein termed residual excitation light). For example, the exemplary dichroic spectrum 230 indicates that wavelengths between 545 nm and 565 nm are only partially reflected, as the dichroic spectrum transitions from substantial reflection to substantial transmission in this range. The shaded region 240 represents residual excitation light, which typically has an intensity of about 1% that of the original excitation light, or about one thousandth that of the illumination source. This light is typically filtered out by an emission filter 170. In the present calibration technique, described further below, this light is used to advantage and measured to calibrate fluorescence detection.

Figure 3:
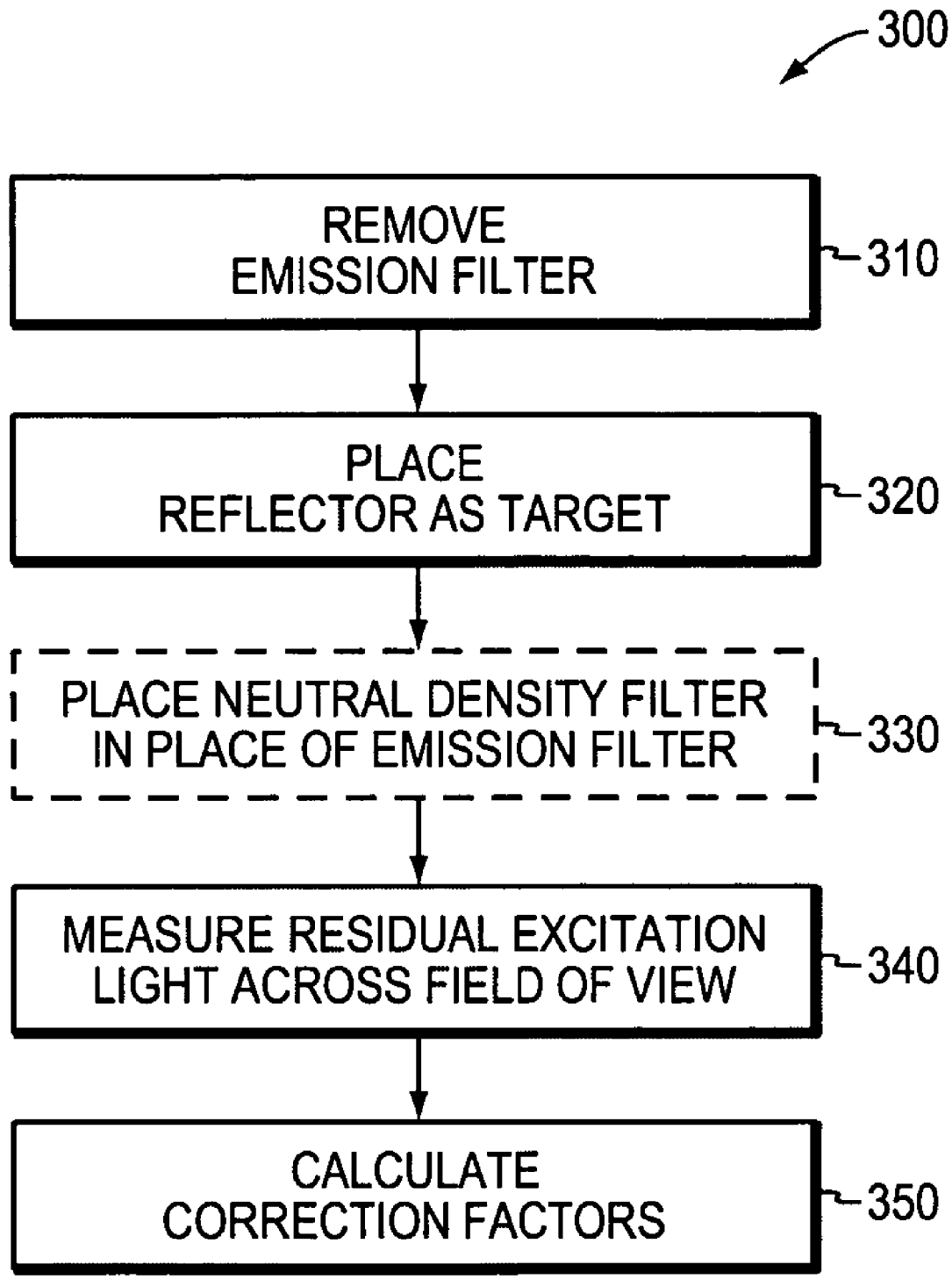
FIG. 3 is a flow chart of a procedure to measure and calibrate fluorescence detection across a field of view of a fluorescence microscope.

FIG. 3 is a flow chart of a procedure to measure and calibrate fluorescence detection across a field of view of a fluorescence microscope. At step 310 the emission filter 170 of the fluorescence microscope 100 is temporarily removed to allow excitation light reflected from the target to pass there-through. At step 320, a near-perfectly uniform reflector is placed under the microscope as the target. Unlike near-perfectly uniform fluorescent emitters that are exceedingly difficult and costly to manufacture, near-perfectly uniform reflectors are inexpensive, and readily obtainable. One near-perfectly uniform reflector made substantially of polytetrafluoroethylene, is commercially marketed under the name by Spectralon® SRM-990 by Labsphere, Inc. of North Sutton, N.H. Another near-perfectly uniform reflector that may be used is a reflector comprising Barium Sulfate ($BaSO_4$) mixed with a binding agent. In addition to these two examples, it is expressly contemplated that a wide range of other materials that exhibit sufficiently uniform reflection (to a desired level of accuracy) may be advantageously used with the present technique.

At step 330, indicated to present only in some embodiments by the dotted lines, a neutral density filter is installed in the place previously occupied by the emission filter. A neutral density filter reduces light of all wavelengths equally, and is advantageous when exposure time cannot be otherwise controlled to a satisfactory level of accuracy. By reducing that light that passes, the neutral density filter allows a longer than normal (an thus more accurately measurable) exposure time to be used with the present calibration technique.

At step 340, the illumination source is activated and the residual excitation light is measured across the field of view. Since the emission filter has been temporarily removed, the residual excitation light is recorded by an image recording device incorporated into the microscope. For example the image recording device may be a CCD camera, such as a model ST-402ME camera, commercially available from Santa Barbara Instruments Group. It is expressly contemplated that any of a wide variety of image recording devices other than cameras may be used to measure residual excitation light intensity. The image recording device records the intensity of residual excitation light at a large number of points across the field of view, and from each measurement forms a pixel i.e. a small discrete component of a digital image. The digital image created represents a "map" of intensity levels of residual excitation light across the field of view. The "map" of residual excitation light intensity captures errors introduced by variations in the illumination source, the collimating lenses, and the optical path of the microscope. Any errors that would be caused by the emission filter itself (which has been removed) are negligible and thus may be ignored. Alternatively, these errors may be determined independently using well-known techniques. Similarly, any errors introduced by the fact that the excitation and emission light are of differing wavelengths may also be ignored as negligible.

At step 350, a map of "correction factors" is calculated from the "map" of residual excitation light intensity. Each "correction factor" is an individual correction associated with a particular point (pixel of an image) of the field of view, and compensates for irregularities in the microscope that affect that particular point. Since fluorescence emission is related to the intensity of excitation light, the "map" of "correction factors" may be readily produced by scaling the "map" of residual excitation light. In this way, the calibration technique employs measurements of excitation light intensity to calibrate fluorescence detection.

Thereafter the emission filter of the microscope may be replaced and a measurement taken of a desired target. The image produced of the target is adjusted according to the "correction factors" to substantially remove unwanted intensity variations due to irregularities in the microscope. In this way, emission light measurements of targets, after adjustment by the "correction factors," may be accurate to within 1%.

Figure 4:
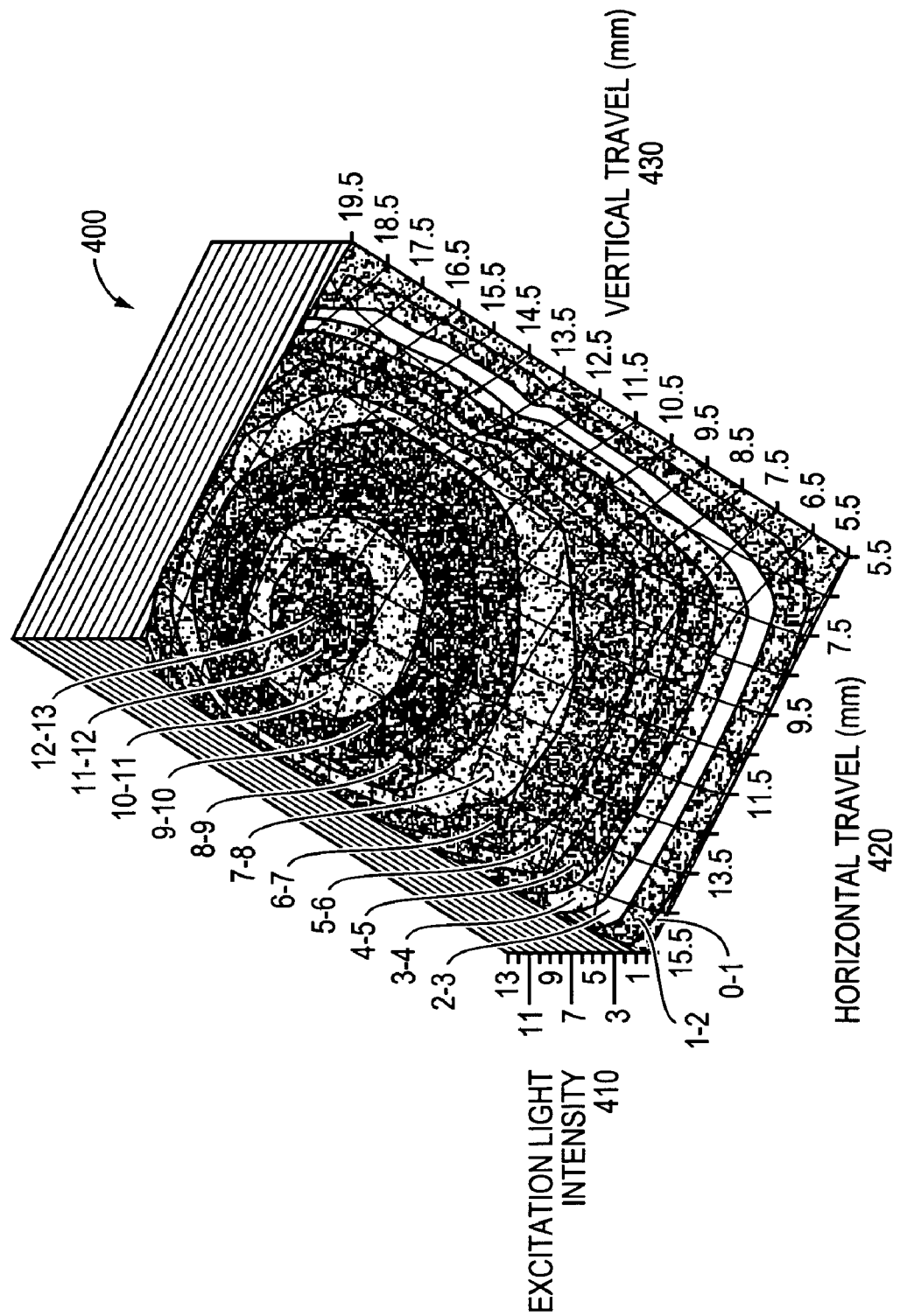
FIG. 4 is a three-dimensional graph illustrating a exemplary "map" of intensity levels of residual excitation light.

FIG. 4 is a three-dimensional graph 400 illustrating an exemplary "map" of intensity levels of residual excitation light. Excitation light intensity is represented in the z-axis 410 and the field of view is represented by the x-y plane formed by x-axis 420 and y-axis 430. Such a "map" may be obtained using the above described technique for measuring residual excitation light intensity levels. Alternatively, such a "map" may be obtained by measuring levels at every location of the field of view using an external fiber-optic apertured coherent power meter or other appropriate measurement device. It is expressly contemplated that, in some application, it may be desirable to verify intensity data obtained by a CCD camera or other image recording device integral to the fluorescence microscope with measurements from an second measurement device. In such way, results may be independently verified and accuracy enhanced.

In another embodiment of the present invention, the above technique may be employed as part of the creation of a control calibration chip. A control calibration chip is a target of robust mechanical and optical properties that is specifically associated with a particular fluorescence microscope. Such a chip may be constructed from any of a wide variety of fluorescent materials. For example, in one embodiment, the chip is made from ordinary paper (which has fluorescent properties), mounted to an appropriately sturdy substrate.

Figure 5:
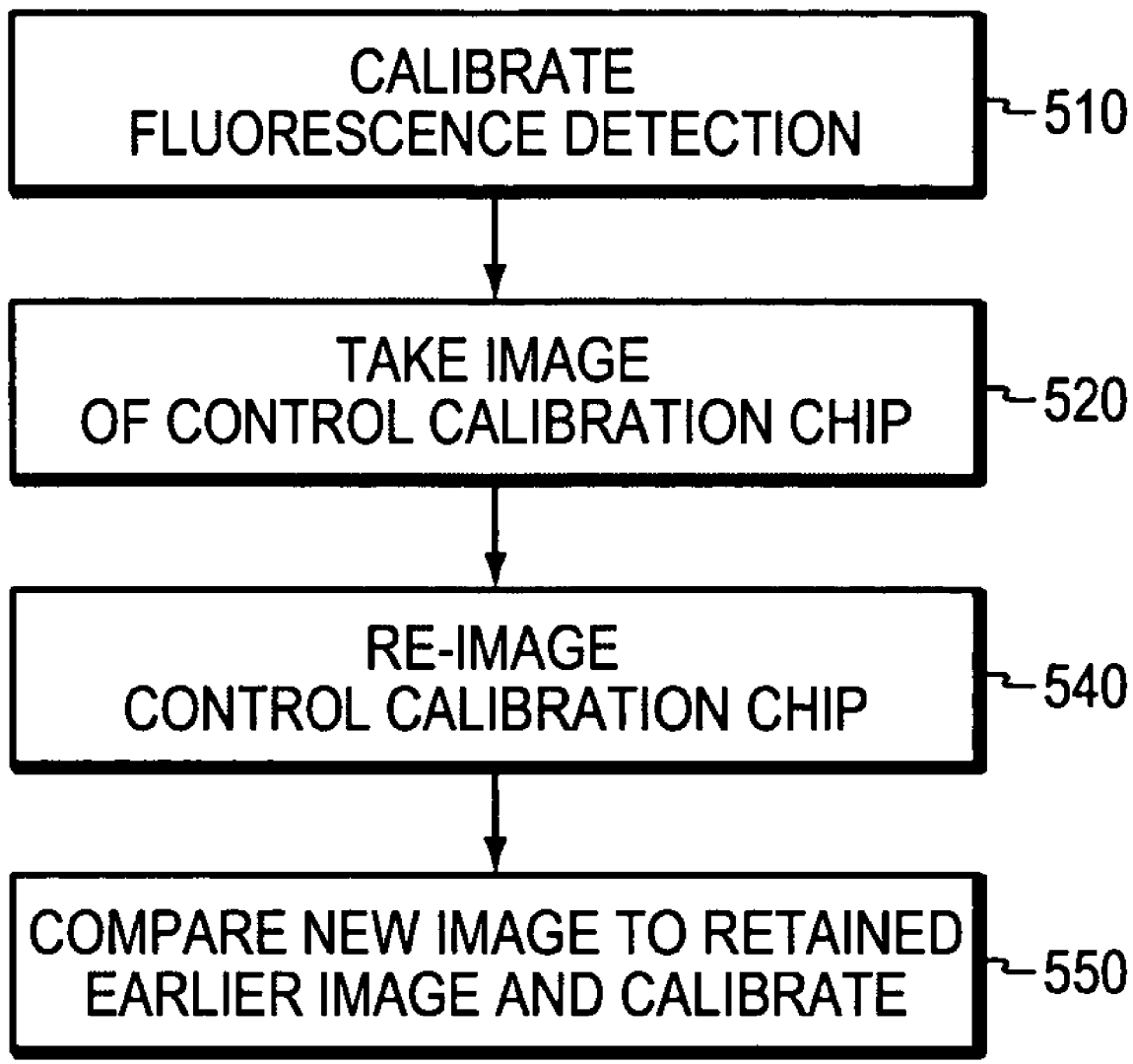
FIG. 5 is a flow chart depicting a method for calibrating emission detection of a fluorescence microscope using a control calibration chip.

FIG. 5 depicts a method for calibrating emission detection of a fluorescence microscope using a control calibration chip. At step 510, a particular florescence microscope is initially calibrated using the method of FIG. 3. Such an initial calibration may be part of a manufacturing process at the factory, conducted by a third-party calibration service, or conducted by the end user. At step 520, an image is taken of the control calibration chip using the calibrated microscope. Such an image is stored digitally in a computer readable media that is retained with the instrument. At a later date, an operator may desire to verify or adjust calibration of the microscope. Accordingly, at step 530, the control calibration chip is re-imaged on the same instrument and a new image is generated. Thereafter, at step 540, the new-image is compared with the retained earlier image and adjustments made to the microscope so the images will substantially coincide.

It is expressly contemplated that the above described techniques may be applied to other types of microscopes, and therefore should not be considered limited to epi-fluorescence microscopes or to closely similar devices. For example, the techniques are applicable to dark-field fluorescence microscopes where oblique illumination (illumination on the order of 15 degrees or more away from the microscope's optical axis) is applied to a target. Darkfield fluorescence microscopes have proven useful in imaging certain targets and have a variety of advantageous applications.

The foregoing has been a detailed description of various illustrative embodiments of the present invention. Further modifications and additions can be made without departing from the invention's intended spirit and scope. It is expressly contemplated that other techniques may be used in conjunction with the above described technique as part of a multi-faceted calibration technique. For example, a variety of known calibration targets may be employed, and calibration data from these targets combined with the calibration data obtained with the above described technique. Further, it is expressly contemplated that any calculations and other processing associated with the present invention may be implemented by a computer system. Therefore, some aspects of the present invention may be embodied in instructions for execution on a processor stored on a computer readable media. Accordingly, it should be remembered that the above descriptions are meant to be taken only by way of example, and not to otherwise limit the scope of this invention.

What is claimed is:

1. A method for calibrating a fluorescence microscope comprising the steps of:
  removing an emission filter from the fluorescence microscope;
  placing a reflector as a target of the fluorescence microscope;
  measuring excitation light reflected by the reflector; and
  adjusting measurements of emission light in response to the measuring of the excitation light.

2. The method of claim 1 further comprising the step of:
  placing a neutral density filter in the optical path of the microscope.

3. The method of claim 2 wherein the neutral density filter is placed at the location previously occupied by the emission filter.

4. The method of claim 1 wherein the reflector is a near-perfectly uniform reflector comprising polytetrafluoroethylene.

5. The method of claim 1 wherein the step of measuring further comprises the step of:
  creating a map of the intensity of the excitation light reflected from the target, the map depicting the intensity at a number of points in the field of view of the fluorescence microscope.

6. The method of claim 5 wherein each point of the field of view of the fluorescence microscope corresponds to a pixel of a digital image, and the map of the intensity of the excitation light is a digital image.

7. The method of claim 5 wherein the step adjusting measurements of emission light further comprises the steps of:
  calculating a map of correction factors from the map of the intensity of the excitation light; and
  using the correction factors to adjust measurements of emission light at points in the field of view.

8. The method of claim 1 wherein the fluorescence microscope is an epi-flourescence microscope.

9. The method of claim 1 wherein the fluorescence microscope is a dark-field fluorescence microscope.

10. The method of claim 1 further comprising:
  associating the fluorescence microscope with a control calibration chip;
  measuring fluorescence emissions of the control calibration chip to create a baseline measurement; and
  retaining the baseline measurement and the control calibration chip with the microscope.

11. The method of claim 1 further comprising:
  comparing a subsequent measurement of the control calibration chip with the baseline measurement, and adjusting the microscope so the subsequent and the baseline measurements will substantially coincide.

12. A system for calibrating fluorescence detection of a microscope comprising:
- a uniform reflector adapted to be used as a target of the microscope;
- a neutral density filter adapted to replace an emission filter of the microscope; and
- a measurement device for measuring the intensity of excitation light reflected by the uniform reflector, through the neutral density filter, at differing points in a field of view of the microscope, the measurement device further adapted to calculate a correction factor at a plurality of points in the field of view, the correction factor for adjusting measurements of emission light.

13. The system of claim 12 wherein the uniform reflector comprises a material containing polytetrafluoroethylene.

14. The system of claim 12 wherein the microscope is an epi-flourescence microscope.

15. The system of claim 12 wherein the microscope is a dark-field fluorescence microscope.

* * * * *